(12) United States Patent
Watanabe et al.

(10) Patent No.: US 6,558,639 B1
(45) Date of Patent: May 6, 2003

(54) APPARATUS AND METHOD FOR PURIFYING FLUIDS INCLUDING CONTAMINANTS

(75) Inventors: Kenji Watanabe, Kasugai (JP); Akira Nagata, Kasugai (JP); Kazushi Nakashima, Kasuagi (JP); Takaaki Katagiri, Kasugai (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/598,698

(22) Filed: Jun. 21, 2000

(30) Foreign Application Priority Data

Jun. 24, 1999 (JP) .......................... 11-178200
Jun. 2, 2000 (JP) ......................... 2000-165898

(51) Int. Cl.[7] ............................................... B01J 19/12
(52) U.S. Cl. .................................. 422/186.3; 210/748
(58) Field of Search ............................ 422/186.3, 186; 210/748; 204/157.15, 157.3

(56) References Cited

U.S. PATENT DOCUMENTS 5,933,702 A * 8/1999 Goswami ................ 422/186.3

6,238,631 B1 * 5/2001 Ogata et al. ............. 422/186.3

FOREIGN PATENT DOCUMENTS

| JP | 6-343875 | | 12/1994 |
| JP | 10-211419 | | 8/1998 |
| JP | 10235202 | * | 8/1998 |
| JP | 10281484 | * | 8/1998 |
| JP | 10-234835 | | 9/1998 |
| JP | 10-235202 | | 9/1998 |
| JP | 10-281484 | | 10/1998 |

* cited by examiner

Primary Examiner—James J. Seidleck
Assistant Examiner—Thao Tran
(74) Attorney, Agent, or Firm—Armstrong, Westerman & Hattori, LLP

(57) ABSTRACT

A purifier for purifying a fluid by eliminating contaminants from the fluid. The purifier includes a fluid passage, through which the fluid flows, formed by an ultraviolet ray transmitting material. A plurality of photocatalytic pipes are arranged in the fluid passage. Each of the photocatalytic pipes has an inner surface and an outer surface on which a thin film of a photocatalyst is applied. The photocatalytic thin film is excited by ultraviolet rays irradiated from a source located near the fluid passage. This oxides and decomposes the contaminants and purifies the fluid.

18 Claims, 8 Drawing Sheets

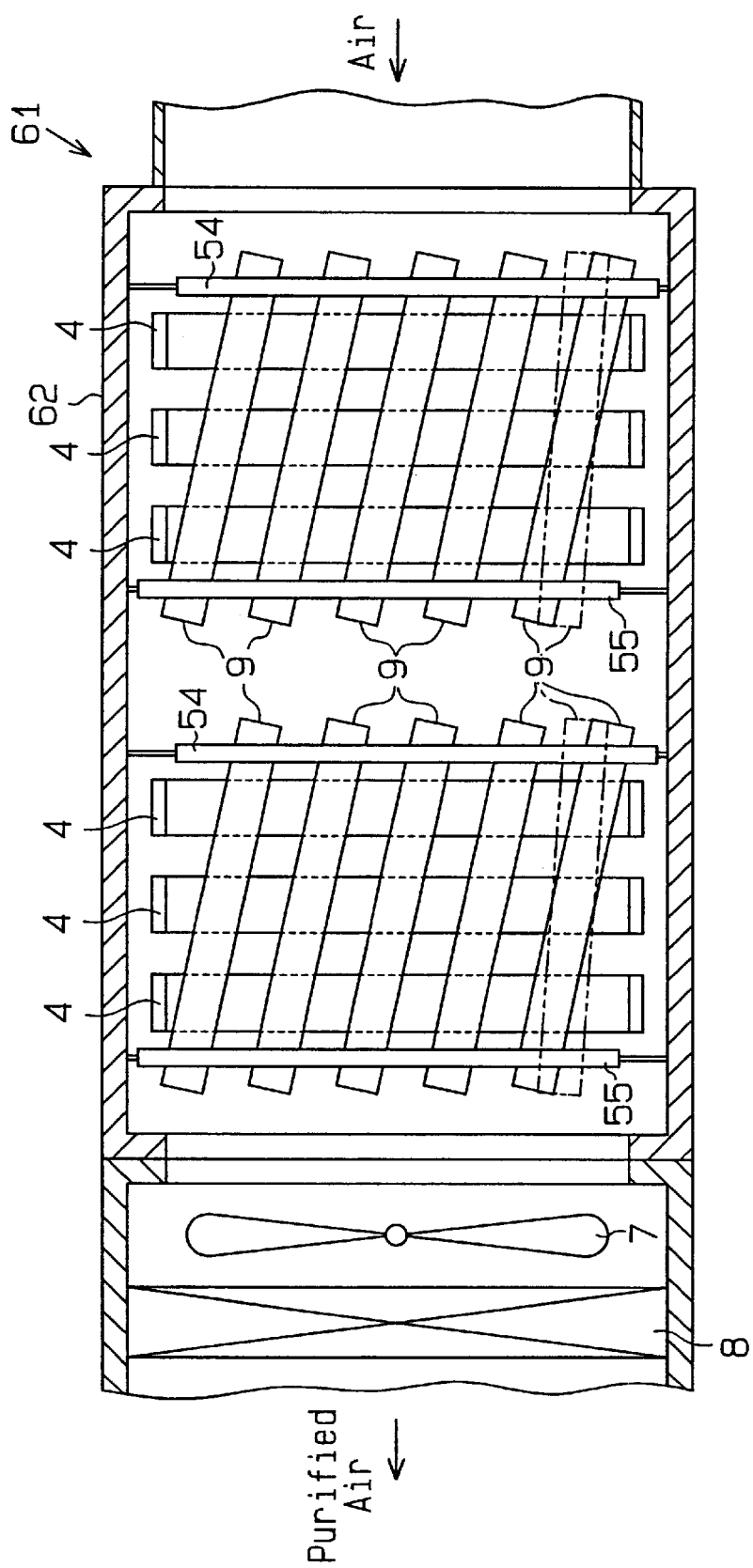

APPARATUS AND METHOD FOR PURIFYING FLUIDS INCLUDING CONTAMINANTS

BACKGROUND OF THE INVENTION

The present invention relates to an apparatus and method for purifying fluids including contaminants, and more particularly, to an apparatus and method for purifying fluids by eliminating airborne molecular contaminants(AMCs) with a photocatalyst.

During the fabrication of ULSI devices, the scale of integration of which is equal to or higher than 64 M (megabit) DRAMs, and the fabrication of LCD devices, fine contaminants that cannot be eliminated by a high performance filter (hereafter referred to as ultra low penetration air (ULPA) filter) may result in the fabrication of deficient ULSI and LCD devices.

The contaminants, which are airborne molecular contaminants, include, for example, organic gas and ammonia gas produced in the fabrication facility. The airborne molecular contaminants are eliminated by a purification apparatus, which uses an adsorbent formed from activated carbon, ion exchange resin, or the like.

FIG. 1 is a schematic diagram showing a prior art air purifier 91. The air purifier 91 is installed in, for example, the ceiling of a clean room, in which semiconductor devices are fabricated, to purify the air in the clean room.

The air purifier 91 includes a chemical filter 92, which eliminates airborne molecular contaminants, and an ULPA filter 93 for eliminating fine particles. A fan 94 is arranged between the chemical filter 92 and the ULPA filter 93. When the fan 94 is driven, the air in the clean room is drawn through the chemical filter 92 and the ULPA filter 93. This eliminates the airborne molecular contaminants and fine particles from the air. The purified air is then returned to the clean room.

The chemical filter 92 is formed by applying activated carbon or a reactive liquid (acid, base, catalyst component, or the like) based on activated carbon to a base material. When the adsorbed contaminant saturates the filter 92, the filter 92 must be replaced. Thus, new filters are needed, which requires maintenance procedures. In addition, the chemical filter 92, which is disposed of as waste, increases costs.

In comparison, a clean air purifier that uses a photocatalyst and does not produce waste is known. A typical photocatalyst is made of, for example, titanium dioxide($TiO_2$) and causes photocatalysis. In other words, when irradiated with ultraviolet rays, the photocatalyst is excited. This oxides and decomposes the airborne molecular contaminants. Air purifiers using a photocatalyst have recently been applied to normal household air-conditioners. In such air purifiers, the photocatalyst is irradiated with ultraviolet rays and air is drawn through the irradiated photocatalyst to decompose contaminants, such as material having an odor, that are suspended in air.

In the air purifier, ozone produced near the source of the ultraviolet rays mixes with the purified air. The ozone enhances oxidation at the surface of wafers used for semiconductor devices. Accordingly, an oxide film forms on a semiconductor wafer due to the ozone. This degrades the device characteristics, decreases the product quality, and decreases the yield.

Japanese Unexamined Patent Publication No. 10-234835 describes a second example of an air purifier in which a photocatalyst is included in an air filter. The air filter is mainly made of glass fiber. In this air purifier, the air filter is irradiated by a light source located in an air passage or located beside the air filter to excite the photocatalyst of the air filter and purify air.

However, in this air purifier, the ultraviolet rays irradiated from the light source are diffused in the air filter. Thus, the photocatalyst may not be excited at locations relatively far from the light source.

SUMMARY OF THE INVENTION

It is an object of the present invention to provide an apparatus and method for efficiently eliminating airborne molecular contaminants through photocatalysis without mixing ozone, which is produced by ultraviolet rays, in the treated fluid.

To achieve the above object, the present invention provides a purifying apparatus for purifying a fluid. The apparatus includes a fluid passage, through which the fluid flows, formed by an ultraviolet ray transmitting material, and a plurality of photocatalytic pipes arranged in the fluid passage. Each of the photocatalytic pipes has an inner surface and an outer surface on which a thin film of a photocatalyst is applied. The photocatalytic thin film is excited by ultraviolet rays irradiated from a location proximal to the fluid passage.

A second aspect of the present invention provides a purifying apparatus for purifying a fluid. The apparatus includes a fluid passage through which the fluid flows. A plurality of photocatalytic pipes are arranged in the fluid passage. Each of the photocatalytic pipes is inclined by a predetermined angle relative to a direction in which the fluid flows and has an inner surface on which a thin film of a photocatalyst is applied. The photocatalytic thin film is excited by ultraviolet rays irradiated from a location proximal to the photocatalytic pipes.

A third aspect of the present invention provides a method for purifying a fluid in a fluid passage. The method includes locating a plurality of photocatalytic pipes in the fluid passage. Each of the photocatalytic pipes has an inner surface and an outer surface to which a thin film of a photocatalyst is applied. The method also includes exciting the photocatalyst by irradiating the catalytic pipes with ultraviolet rays, and conveying the fluid through the fluid passage so that the fluid contacts the excited photocatalyst.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which:

FIG. 10 is a partial cross-sectional view schematically showing an air purifier according to a seventh embodiment of the present invention.

DETAILED DESCRIPTION OF THE PREFERRED EMBODIMENTS

[First Embodiment]

Figure 1:
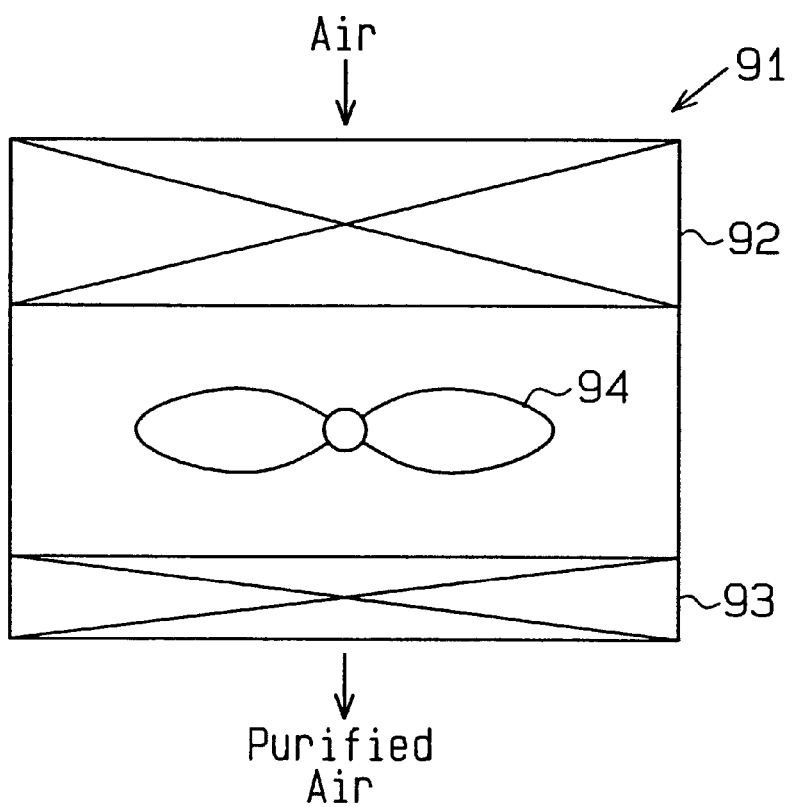
FIG. 1 is a schematic diagram showing a prior art air purifier.

In the drawings, like numerals are used for like elements throughout.

Figure 2:
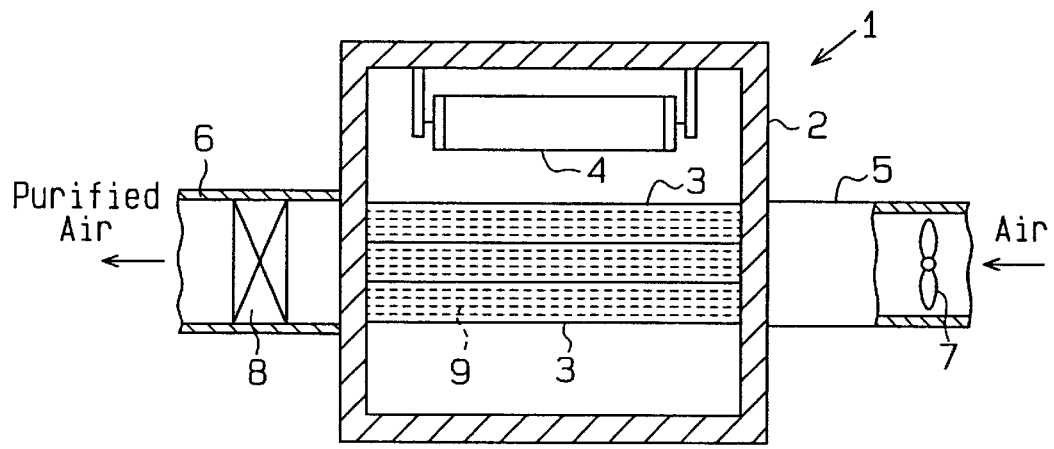
FIG. 2 is a partial cross-sectional view showing an air purifier according to a first embodiment of the present invention.

FIG. 2 is a schematic cross-sectional view showing an air purifier (purifying apparatus) 1 according to a first embodiment of the present invention.

The air purifier 1 is preferably installed in a wall of a clean room and located in an air passage through which the air of the clean room is circulated. The air purifier 1 purifies the air (treated fluid) passing through the passage. Further, the air purifier 1 may also be installed at other locations, such as in the ceiling or the floor of the clean room.

The air purifier 1 includes a plurality of outer pipes (retaining pipes) 3, which serves as a fluid passage, and an ultraviolet lamp 4, which is located near the outer pipes 3 and serves as an ultraviolet ray irradiation unit. The outer pipes 3 and the ultraviolet lamp 4 are arranged in a purification box 2. The air purifier 1 eliminates the airborne molecular contaminants suspended in the air that is sent through an upstream pipe 5 from the clean room and returns the purified air to the clean room through a downstream pipe 6.

Figure 3:
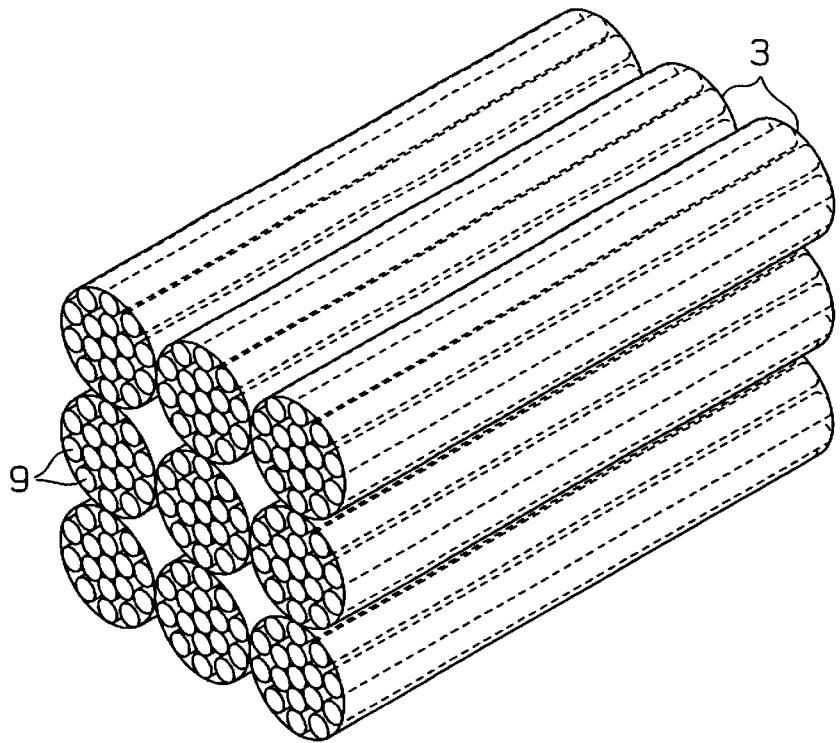
FIG. 3 is a perspective view showing outer pipes and inner pipes of the air purifier of FIG. 2.

As shown in FIG. 3, the outer pipes 3, which are tubular, extend in the air flow direction and are arranged to form, for example, a grid-like array. A fan 7, which is located in the upstream pipe 5, draws air into each of the outer pipes 3.

A ULPA filter 8 for eliminating the fine particles suspended in the air is arranged in the downstream pipe 6. The ULPA filter 8 may also be located upstream of the outer pipes 3.

Figure 4:
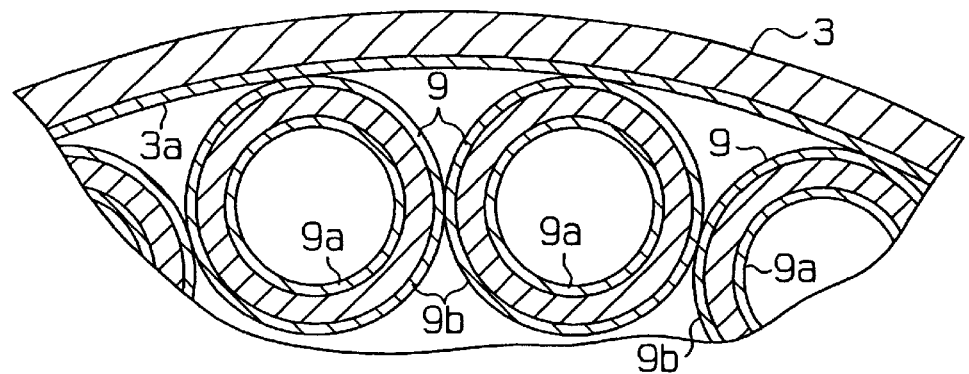
FIG. 4 is an enlarged cross-sectional view showing the outer and inner pipes of FIG. 3.

As shown in FIG. 4, a thin film 3a of a photocatalyst is formed on the inner surface of each outer pipe 3. Referring to FIG. 3, a plurality of transparent inner pipes 9 (each having a diameter of, for example, ten millimeters) extend through each outer pipe 3. As shown in FIG. 4, thin films 9a, 9b of a photocatalyst are formed respectively on the inner and outer surfaces of each inner pipe (photocatalyst pipe) 9. In the first embodiment, titanium dioxide is used as the photocatalyst. In other words, the thin films 3a, 9a, 9b applied to the inner surfaces of the outer pipes 3, and the inner and outer surfaces of the inner pipes 9, respectively, are formed from titanium dioxide. More specifically, the inner pipes 9 are produced by coating the inner and outer surfaces of transparent glass pipes with a sol in which fine particles of titanium dioxide are dispersed. The glass pipes are then heat treated, which results in a uniform titanium dioxide film (a thin film having a thickness of about 1 micrometer) having an anatase crystal structure being deposited on the inner and outer surfaces.

The ultraviolet lamp 4, which is a linear tube arranged parallel to the outer pipes 3, efficiently irradiates all of the outer pipes 3 with ultraviolet rays. The excitation of the photocatalytic thin films 3a, 9a, 9b, when irradiated with the ultraviolet rays from the ultraviolet lamp 4, oxides and decomposes the airborne molecular contaminants suspended in the air. It is preferred that the ultraviolet lamp 4 irradiate ultraviolet rays having a wavelength band included in the range of 150 to 450 nm, which is optimal for exciting the photocatalyst. In the first embodiment, the ultraviolet lamp 4 irradiates ultraviolet rays having a median wavelength of 350nm. Alternatively, ultraviolet rays having a median wavelength of 180 nm or 280 nm may also be irradiated.

It is preferred that the outer and inner pipes 3, 9 be made of glass having a high ultraviolet ray transmittance. Further, the thin films 3a, 9a, 9b have a predetermined ultraviolet ray transmittance that is determined in accordance with their thickness. The titanium dioxide thin films 3a, 9a, 9b formed in this manner cause photocatalysis along the entire inner surfaces of the outer pipes 3 and along the entire inner and outer surfaces of the inner pipes 9.

Each of the outer pipes 3 is connected to the upstream and downstream pipes 5, 6 by couplers (not shown) so that the air in the purification box 2 does not mix with the air flowing through the air passage. In other words, the air passing through the outer pipes 3 is separated from the air outside the outer pipes 3. Therefore, the air from the clean room does not leak from the outer pipes 3 and flows through air passages formed in each of the inner pipes 9 and through air passages formed between the outer surfaces of the inner pipes 9 and the inner surfaces of the associated outer pipes 3. When the flowing air contacts the inner surfaces of the outer pipes 3 and the inner and outer surfaces of the inner pipes 9, photocatalysis occurs. This oxidizes and decomposes the airborne molecular contaminants.

The operation of the air purifier 1 will now be discussed.

When the ultraviolet lamp 4 irradiates the outer pipes 3 with ultraviolet rays, the photocatalyst applied to the inner surfaces of the outer pipes 3 and the inner and outer surfaces of the inner pipes 9 is excited. More specifically, the ultraviolet rays transmitted by the outer pipes 3 excite the photocatalytic thin film 3a applied to the inner surfaces of the outer pipes 3. After passing through the outer pipes 3, the ultraviolet rays excite the photocatalytic thin films 9b applied to the outer surfaces of the inner pipes 9. Some of the ultraviolet rays are transmitted by the inner pipes 9 and excite the photocatalytic thin films 9a applied to the inner surfaces of the inner pipes 9. In this manner, the ultraviolet rays efficiently excite the photocatalytic thin films 3a, 9a, 9b.

The fan 7 is then driven to draw air into the outer pipes 3 through the upstream pipe 5 from the clean room. The drawn in air contacts the inner surfaces of the outer pipes 3 and the inner and outer surfaces of the inner pipes 9 as it flows. The air contacts the photocatalytic thin films 3a, 9a, 9b excited by the ultraviolet rays. The airborne molecular contaminants suspended in the air are decomposed when they contact the excited photocatalytic thin films 3a, 9a, 9b.

The air flows through the outer pipes 3 and to the ULPA filter 8, which separates fine particles from the air. The purified air is then returned to the clean room through the downstream pipe 6. In this manner, the air purifier 1 eliminates airborne molecular contaminants and fine particles from the air of the clean room.

The air purifier 1 of the first embodiment has the advantages described below.

(1) The photocatalysts (titanium dioxide thin film) 3a, 9a, 9b are efficiently excited by the ultraviolet rays from the ultraviolet lamp 4. As the air from the clean room flows through the outer pipes 3, the airborne molecular contaminants are oxidized and decomposed efficiently by contact with the thin films 3a, 9a, 9b. Thus, the contaminants suspended in the air are eliminated efficiently.

(2) The outer pipes 3 separate the space about the ultraviolet lamp 4 from the space through which the air to be treated flows. This prevents the ozone produced near the ultraviolet lamp 4 from mixing with the purified air. Accordingly, even if semiconductor wafers are stored in or semiconductor devices are fabricated in the air purified by the air purifier 1, the semiconductor wafers are not contaminated by airborne molecular contaminants. Further, the growth of native oxide due to ozone is inhibited. This improves the quality of the semiconductor devices and increases the fabrication yield.

(3) Since the airborne molecular contaminants in the air are oxidized and decomposed by the photocatalysts, the outer and inner pipes 3, 9 need not be replaced. Further, the outer and inner pipes 3, 9 are not easily stained by photocatalysis. If the outer and inner pipes 3, 9 become stained, photocatalysis weakens the bonding of the stains and facilitates their removal. For example, the stains may be easily washed off with water. This reduces maintenance costs. Further, the air purifier 1 does not harm the environment, since it decomposes and eliminates contaminants.

(4) In the air purifier 1 of the first embodiment, the ultraviolet lamp 4 is not located in the passage through which air flows. This improves the air circulation efficiency and increases the air purification capability.

(5) The inner pipes 9 are formed from transparent tubular glass pipes. The glass pipes are dipped into a titanium dioxide sol and baked to form a titanium dioxide thin film having a uniform thickness on the inner and outer surfaces of the inner pipes 9. The inner pipes 9 are located in the corresponding outer pipe 3 to form an air passage in which airborne molecular contaminants are oxidized and decomposed. Accordingly, the air purifier 1 of the first embodiment has a simple structure that facilitates manufacture and reduces costs.

[Second Embodiment]

Figure 5:
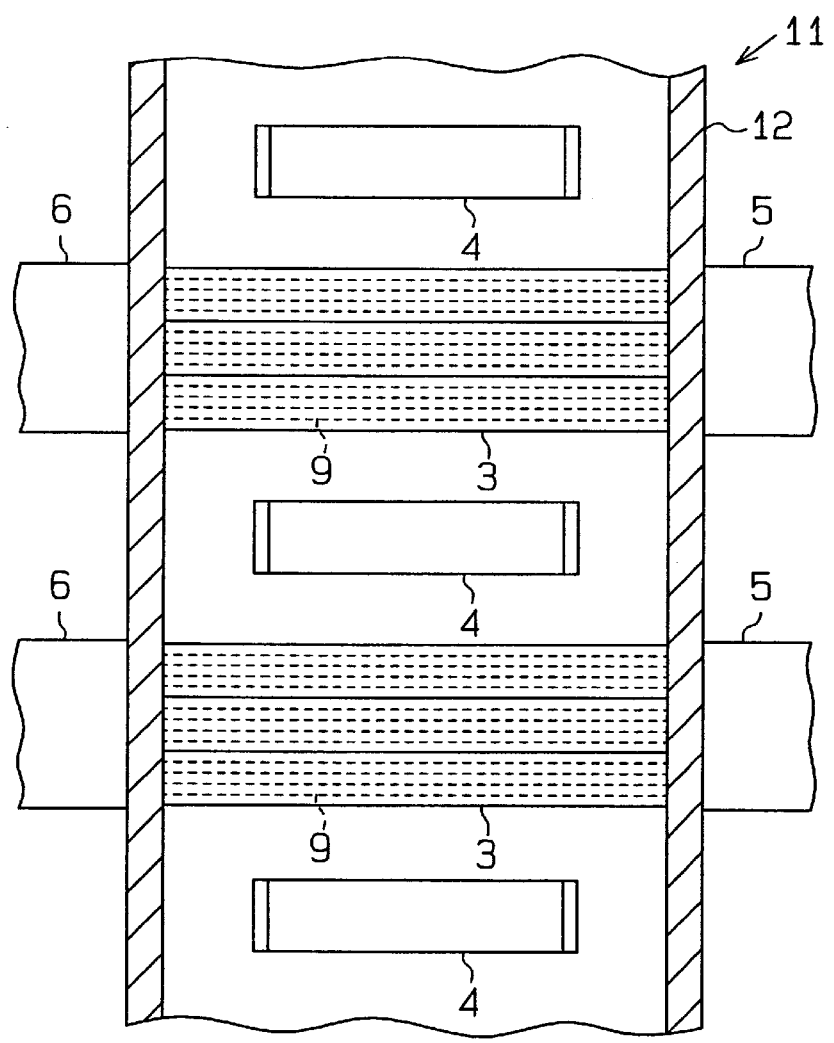
FIG. 5 is a partial cross-sectional view schematically showing an air purifier according to a second embodiment of the present invention.

FIG. 5 is a schematic diagram showing an air purifier 11 according to a second embodiment of the present invention.

As shown in FIG. 5, groups of the outer pipes 3 and a plurality of the ultraviolet lamps 4 are arranged alternately in a purification box 12. Although not shown in FIG. 5, a fan similar to that used in the first embodiment is arranged upstream of the outer pipes 3, and a ULPA filter similar to that used in the first embodiment is arranged downstream of the outer pipes 3.

In the second embodiment, each group of the outer pipes 3 is irradiated with ultraviolet rays from two sides. Thus, the amount of ultraviolet rays irradiating the photocatalytic thin films 3a, 9a, 9b is increased. In other words, excitation of the photocatalysts is improved and the purification efficiency of the airborne molecular contaminants is improved. Further, the increased number of the outer pipes 3 increases the air flow rate. This increases the treating capacity of the air purifier 11.

[Third Embodiment]

Figure 6:
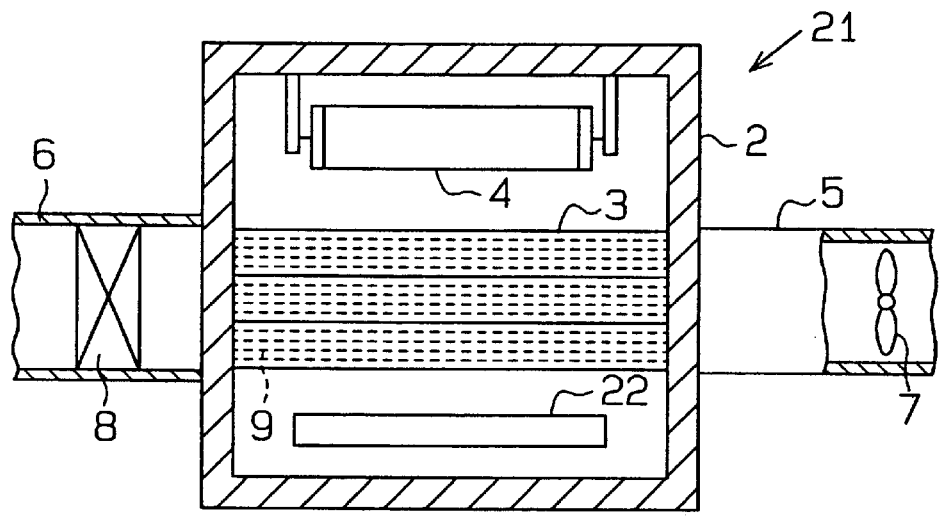
FIG. 6 is a partial cross-sectional view schematically showing an air purifier according to a third embodiment of the present invention.

FIG. 6 is a schematic diagram showing an air purifier 21 according to a third embodiment of the present invention.

The air purifier 21 of the third embodiment is effective when space for locating an ultraviolet lamp 4 on each side of the outer pipes 3 is not available.

As shown in FIG. 6, the air purifier 21 includes a mirror 22, which serves as an ultraviolet ray reflector. More specifically, the ultraviolet lamp 4 and the mirror 22 are located at opposite sides of the outer pipes 3.

When the ultraviolet lamp 4 irradiates the outer pipes 3 with ultraviolet rays, the ultraviolet rays passing through the outer pipes 3 and the ultraviolet rays reflected by the inner walls of the purification box 2 are reflected by the mirror 22. The ultraviolet rays reflected by the mirror 22 irradiate the outer pipes 3. This improves excitation of the photocatalysts at the inner surface of the outer pipes 3 and the inner and outer surfaces of the inner pipes 9.

In the air purifier 21 of the third embodiment, the mirror 22 efficiently irradiates the photocatalytic thin films 3a, 9a, 9b with ultraviolet rays even if the available space is relatively small. Thus, the air purifier 21 is compact but has a high purification efficiency. Further, the ultraviolet rays are efficiently used by the photocatalysts. Thus, the air purifier 21 saves power.

[Fourth Embodiment]

Figure 7:
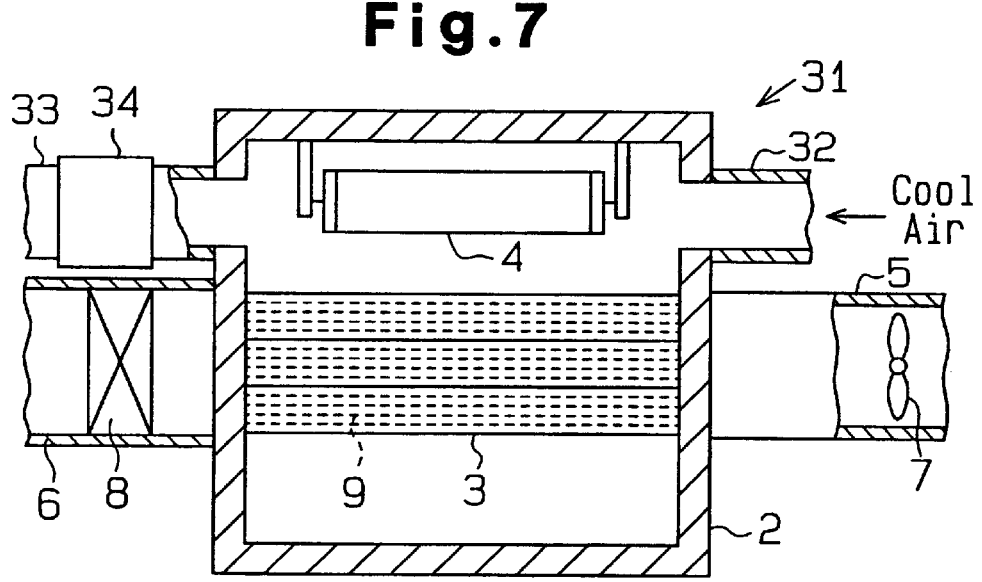
FIG. 7 is a partial cross-sectional view schematically showing an air purifier according to a fourth embodiment of the present invention.

FIG. 7 is a schematic diagram showing an air purifier 31 according to a fourth embodiment of the present invention. The air purifier 31 of the fourth embodiment has a cooling mechanism for cooling the ultraviolet lamp 4.

A supply passage 32 and a discharge passage 33 are connected to the purification box 2 above the pipes 5, 6. Cool air is drawn into the purification box 2 through the supply passage 32 to cool the ultraviolet lamp 4. The cooling air is then discharged through the discharge passage 33. An ozone decomposing device 34 is arranged in the discharge passage 33 to decompose the ozone produced near the ultraviolet lamp 4 and eliminate the ozone from the air. The supply passage 32 and the discharge passage 33 form the cooling mechanism.

The air purifier 31 of the fourth embodiment has the advantage of reducing the temperature of the ultraviolet lamp 4 with the cooling mechanism. This decreases the occurrence of malfunctions in the ultraviolet lamp 4 that may be caused by heat. Further, the ozone produced near the ultraviolet lamp 4 is discharged through the discharge passage 33 with the cool air. This decreases the ozone concentration in the purification box 2. As a result, the absorption of ultraviolet rays by the ozone is decreased and the outer pipes 3 are irradiated by a greater amount of ultraviolet rays. Accordingly, the purification efficiency of the air purifier 31 is improved.

[Fifth Embodiment]

Figure 8:
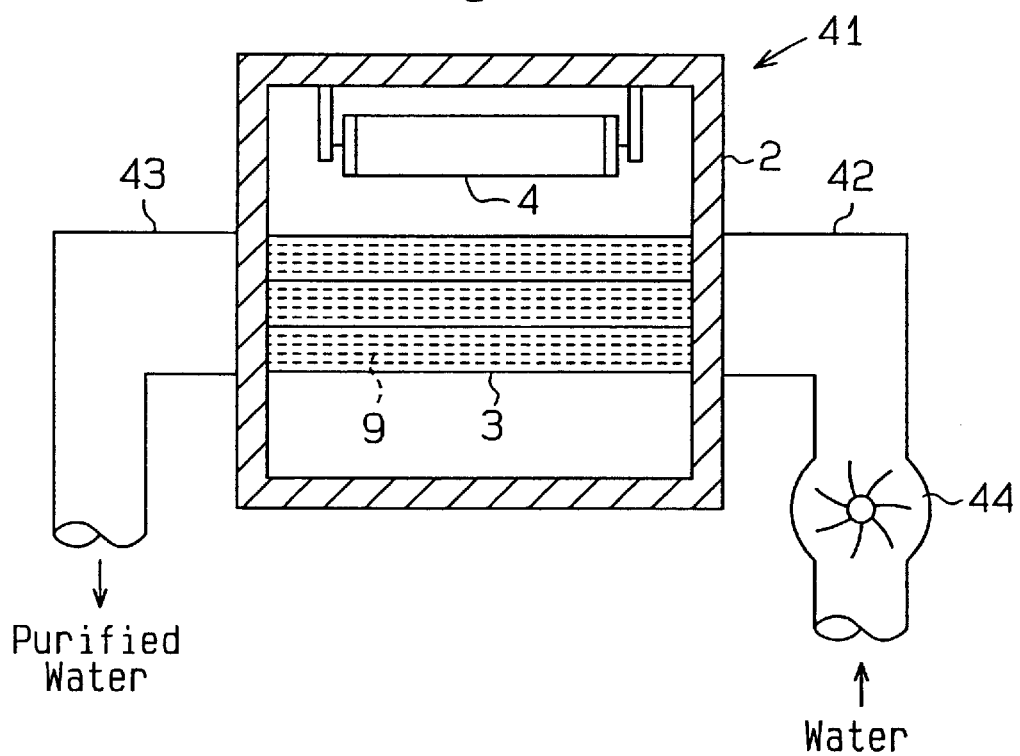
FIG. 8 is a partial cross-sectional view schematically showing a liquid purifier according to a fifth embodiment of the present invention.

FIG. 8 is a schematic diagram showing a liquid purifier 41 according to a fifth embodiment of the present invention. The liquid purifier 41 of the fifth embodiment purifies the airborne molecular contaminants included in washing water, which is used, for example, during the fabrication of semiconductor devices.

As shown in FIG. 8, the outer pipes 3 are connected to an upstream pipe 42 and a downstream pipe 43. A pump 44 is arranged in the upstream pipe 42. The upstream pipe 42, the outer pipes 3, and the downstream pipe 43 form a fluid passage. The pump 44 is driven so that the washing water flows from the upstream pipe 42 to the outer pipes 3 and then to the downstream pipe 43.

As the washing water flows through the outer pipes 3, photocatalysis occurs, and the airborne molecular contaminants in the washing water, which contacts the titanium dioxide thin films 3a, 9a, 9b formed on the inner surfaces of the outer pipes 3 and the inner and outer surfaces of the inner pipes 9, are oxidized and decomposed. The washing water includes water and a washing liquid.

In the fifth embodiment of the liquid purifier 41, the airborne molecular contaminants included in the washing water are decomposed efficiently. Further, the self-cleaning characteristic of the photocatalyst prevents the outer and inner pipes 3, 9 from being stained. This reduces maintenance costs of the liquid purifier 41.

[Sixth Embodiment]

Figure 9A:
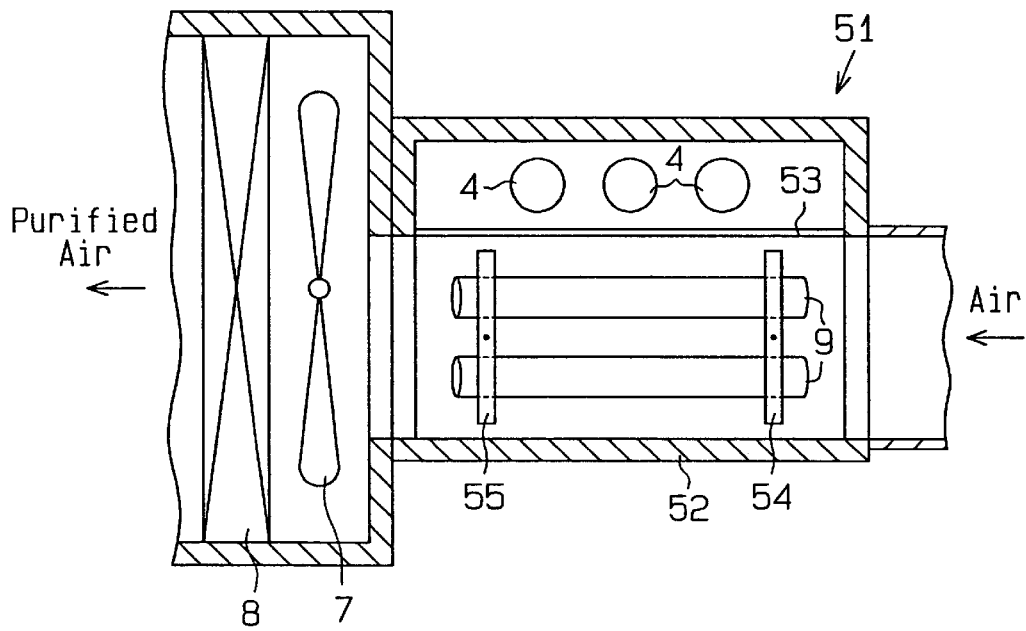
FIG. 9(a) is a partial cross-sectional plan view schematically showing an air purifier according to a sixth embodiment of the present invention.
Figure 9B:
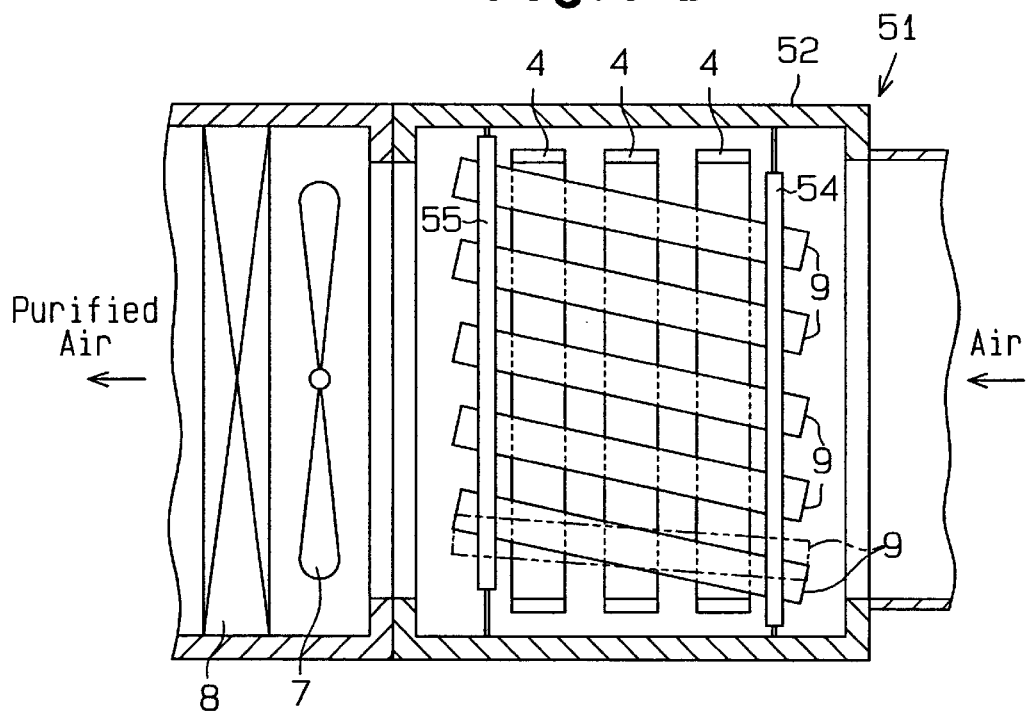
FIG. 9(b) is a cross-sectional side view showing the apparatus of FIG. 9(a)

FIG. 9(a) is a schematic cross-sectional plan view showing an air purifier 51 according to a sixth embodiment of the present invention. FIG. 9(b) is a cross-sectional side view of the air purifier 51 of FIG. 9(a).

The air purifier 51 includes a plurality of ultraviolet lamps 4 and a plurality of purifying pipes (which correspond to the inner pipes of the first embodiment) 9 located in a purification box 52. A partition 53 divides the purification box 52 into a lamp chamber, in which the ultraviolet lamps 4 are accommodated, and a fluid passage, through which air flows. Accordingly, the partition 53 separates the air about the ultraviolet lamps 4 from the space in which air is treated.

The purifying pipes 9 are supported by first and second supports 54, 55 so that the pipes 9 are parallel. Further, the purifying pipes 9 are inclined by a predetermined angle relative to the direction in which air flows, as shown in FIG. 9(b). The supports 54, 55 support the purifying pipes 9 so that the pipes 9 may be moved between a first position, in which the axes of the pipes 9 are parallel to the axis of the air flow passage, and a second position, in which the axes of the pipes 9 are inclined by a predetermined angle relative to the axis of the air flow passage. The air contacts the photocatalytic thin films 9a, 9b, which are formed on the inner and outer surfaces of the purifying pipes 9.

By moving at least one of the first and second supports 54, 55 in a direction perpendicular to the air flow direction, the angle of the pipes 9 relative to the axis of the air flow passage varies as shown by the broken line in FIG. 9(b). Although FIG. 9(b) shows the movement of only one of the purifying pipes 9, the other pipes 9 are moved in the same manner.

The axis of each of the ultraviolet lamps 4 is transverse to the axes of the purifying pipes 9, or transverse to the air flow direction. The lamp arrangement efficiently excites the photocatalysts of the thin films 9a, 9b formed on the inner and outer surfaces of the purifying pipes 9.

In the air purifier of the sixth embodiment, the inclination of the purifying pipes 9 by a predetermined angle relative to the air flow direction changes the angle of incidence between the flowing air and the photocatalysts applied to the inner and outer surfaces of the purifying pipes 9. This purifies air efficiently.

Furthermore, by changing the angle of the purifying pipes 9 relative to the air flow direction, air efficiently contacts the photocatalysts and improves the air purification efficiency.

[Seventh Embodiment]

FIG. 10 is a schematic diagram showing an air purifier 61 according to a seventh embodiment of the present invention.

As shown in FIG. 10, the air purifier 61 includes a plurality of purifying pipes 9 connected to first and second supports 54, 55 in a purification box 62. The purifying pipes 9 are arranged in groups (two groups in this embodiment), one group being downstream of the other. The inclination of the purifying pipes 9 in each group relative to the axis of the air flow passage is changed by the associated first and second supports 54, 55.

In the air purifier 61 of the seventh embodiment, the two groups of purifying pipes 9 increase the surface area of the photocatalytic thin films 9a, 9b (in comparison to one group of that size). In other words, the area of contact between air and the photocatalysts increases. As a result, the capability for purifying air by eliminating airborne molecular contaminants increases.

In the seventh embodiment, a plurality of the purification boxes 52 shown in FIG. 9 may be located serially in the air flow passage. Further, in the seventh embodiment, the direction of inclination of the purifying pipes 9 in one group may differ from that of the purifying pipes 9 in the other group.

It should be apparent to those skilled in the art that the present invention may be embodied in many other specific forms without departing from the spirit or scope of the invention. Particularly, it should be understood that the present invention may be embodied in the following forms.

The photocatalyst may be made of any material that causes photocatalysis. However, titanium dioxide is preferred since it reacts to a small amount of ultraviolet rays.

The photocatalytic thin films (titanium dioxide thin films) 3a applied to the inner surfaces of the outer pipes 3 may be omitted. However, it is preferred that the photocatalytic thin films 3a be formed to improve the purifying efficiency of the treated fluid.

It is preferred that the fluid passage be separated from the space in which the ultraviolet lamp 29 is arranged by a material that transmits ultraviolet rays to excite photocatalysts. In other words, it is preferred that an ultraviolet ray transmitting material separate the fluid passage from the space about the ultraviolet lamp 4 to prevent the ozone produced about the ultraviolet lamp 4 from entering the fluid passage.

The outer and inner pipes 3, 9 may be made of normal glass in accordance with the wavelength of the ultraviolet ray of the ultraviolet lamp 4. The pipes 3, 9 may be made of a material, such as resin, that transmits ultraviolet rays. The outer and inner pipes 3, 9 need only be made of a material that transmits ultraviolet rays.

The shape and number of the outer and inner pipes 3, 9 and the thickness of the photocatalyst films may be changed as required in accordance with the ultraviolet ray transmittance when fluid is flowing.

The ultraviolet lamp 4 may be accommodated in a box made of a material that transmits ultraviolet rays and the lamp box may be connected to a purification box.

An ultraviolet lamp that irradiates ultraviolet rays having a median wavelength of 368 nm may be used. The amount of ozone produced by such ultraviolet lamp is relatively small. In this case, the space about the ultraviolet lamp need not be separated from the fluid passage. This would simplify the structure of the purifiers 1, 11, 21, 31, 41, 51, 61.

The air purifiers 1, 11, 21, 31 of the first to fourth embodiments may be applied to, for example, a clean bench or a clean booth arranged in a clean room to locally purify air. If the air purifier is applied to a wafer storage, the ozone produced about the ultraviolet lamp is prevented from being included in wafers.

The fan 7 of the first to fourth embodiments may be arranged in a pipe downstream of the inner pipes 9 like in the sixth and seventh embodiments.

The ozone decomposing device 34 of the fourth embodiment may be omitted. In this case, it is preferred that the air flowing through the discharge passage 33 be discharged at a location that does not affect humans or semiconductor wafers.

Figure 11:
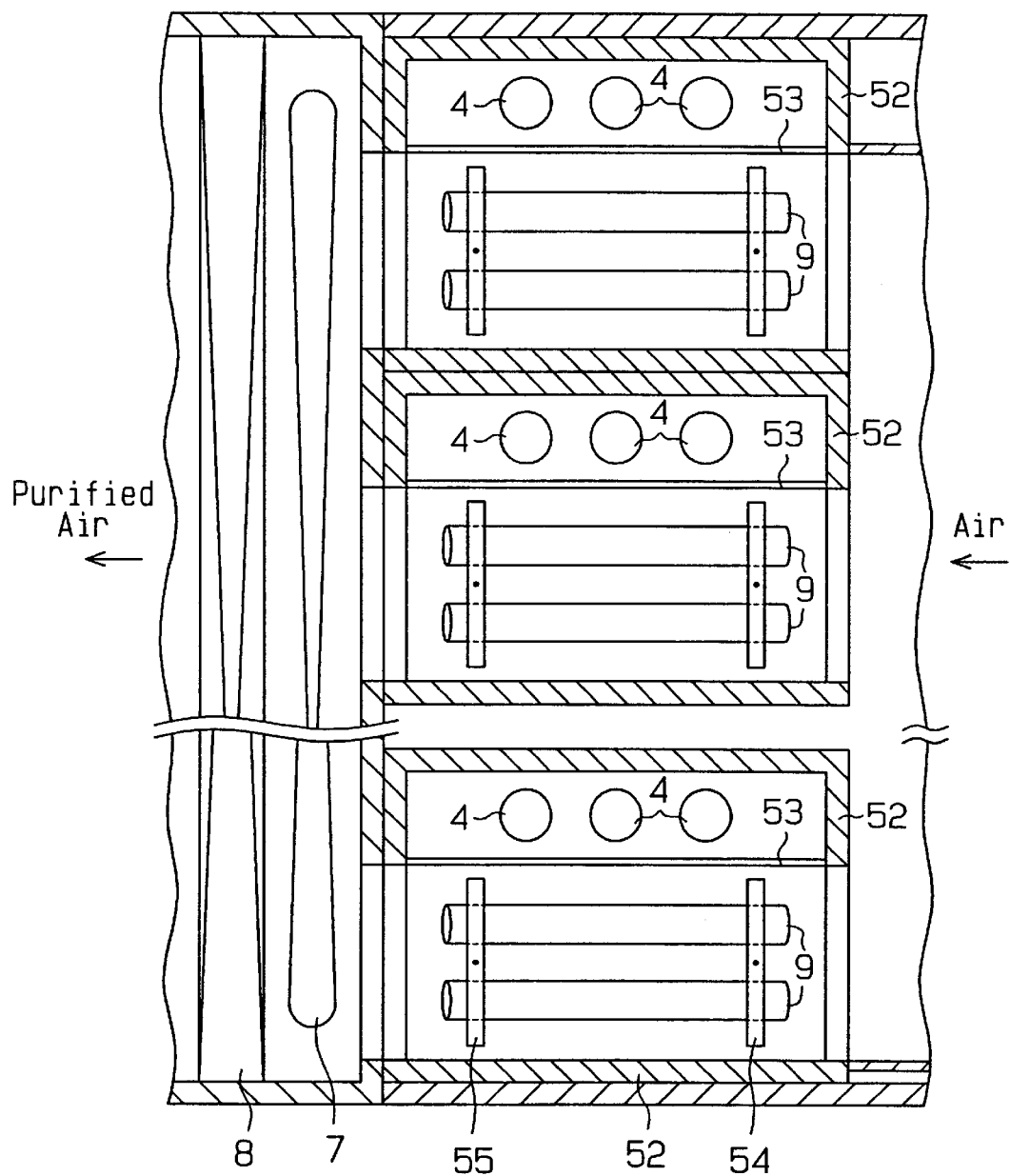
FIG. 11 is a partial cross-sectional view schematically showing an air purifier according to a further embodiment of the present invention.

In the sixth and seventh embodiments, a plurality of the purification boxes 52, 62 may be arranged in a parallel manner, as shown in FIG. 11. This increases the amount of air flowing through the air purifier and increases the purifying capacity of the purifier.

The present examples and embodiments are to be considered as illustrative and not restrictive, and the invention is not to be limited to the details given herein, but may be modified within the scope and equivalence of the appended claims.

What is claimed is:

1. A purifying apparatus for purifying a fluid, comprising:
   an ultraviolet light source;
   an outer pipe located proximal to the ultraviolet light source, the outer pipe transmitting, an ultraviolet ray and defining a fluid passage, and the outer pipe forming a fluid barrier between the fluid passage and ozone generated at the ultraviolet light source; and
   a plurality of photocatalytic pipes provided in the fluid passage, wherein each of the photocatalytic pipes is formed by an ultraviolet ray transmitting material and has an inner surface and an outer surface on which a thin film is Applied being excited by ultraviolet rays irradiated from the ultraviolet light source through the outer pipe.

2. The purifying apparatus according to claim 1, wherein the fluid passage includes a cylindrical retaining pipe for retaining the photocatalytic pipes.

3. The purifying apparatus according to claim 2, wherein the retaining pipe has an inner surface to which a thin film of a photocatalyst is applied.

4. The purifying apparatus according to claim 1, further comprising:
   an ultraviolet ray irradiation unit for irradiating the ultraviolet rays; and
   a cooling mechanism for cooling the ultraviolet ray irradiation unit.

5. The purifying apparatus according to claim 1, wherein the fluid passage is one of a plurality of fluid passages, the apparatus further comprising a plurality of ultraviolet ray irradiation units for irradiating the ultraviolet rays, wherein the fluid passages extend between the ultraviolet ray irradiation units.

6. The purifying apparatus according to claim 5, further comprising a cooling mechanism for cooling the ultraviolet ray irradiation units.

7. The purifying apparatus according to claim 1, further comprising an ultraviolet ray irradiation unit for irradiating the ultraviolet rays, and an ultraviolet ray reflector, wherein the ultraviolet ray irradiation unit and the ultraviolet ray reflector are located on opposite sides of the fluid passage.

8. The purifying apparatus according to claim 7, further comprising a cooling mechanism for cooling the ultraviolet ray irradiation unit.

9. A purifying apparatus for purifying a fluid, comprising:
   an ultraviolet light source;
   an outer pipe located proximal to the ultraviolet light source, the outer pipe transmitting an ultraviolet ray and defining a fluid passage, and the outer pipe forming a fluid barrier between the fluid passage and ozone generated at the ultraviolet light source; and
   a plurality of photocatalytic pipes provided in the fluid passage, wherein each of the photocatalytic pipes is comprised of an ultraviolet ray transmitting material, and is inclined by a predetermined angle relative to a direction in which the fluid flows and has an inner surface and an outer surface on which a thin film of a photocatalyst is applied, the photocatalytic thin film being excited by ultraviolet rays irradiated from the ultraviolet light source.

10. The purifying apparatus according to claim 9, wherein the angle of the photocatalytic pipes relative to the axis of the fluid passage is variable.

11. The purifying apparatus according to claim 9, further comprising:
   a lamp for irradiating the ultraviolet rays; and
   a box including a partition that transmits ultraviolet rays, wherein the partition divides the box into the fluid passage and a chamber for accommodating the lamp.

12. The purifying apparatus according to claim 11, wherein the box is one of a plurality of boxes arranged in a parallel manner.

13. The purifying apparatus according to claim 12, wherein the angle of the photocatalytic pipes relative to the axis of the fluid passage is variable.

14. The purifying apparatus according to claim 11, wherein the angle of the photocatalytic pipes relative to the axis of the fluid passage is variable.

15. The purifying apparatus according to claim 11, wherein the plurality of the photocatalytic pipes includes a first photocatalytic pipe group and a second photocatalytic pipe group arranged serially.

16. The purifying apparatus according to claim 15, wherein the box is one of a plurality of boxes arranged in a parallel manner.

17. The purifying apparatus according to claim 16, wherein the angle of the photocatalytic pipes relative to the axis of the fluid passage is variable.

18. The purifying apparatus according to claim 15, wherein the angle of the first and second photocatalytic pipe groups relative to the axis of the fluid passage is variable.

* * * * *

UNITED STATES PATENT AND TRADEMARK OFFICE
CERTIFICATE OF CORRECTION

PATENT NO. : 6,558,639 B1 Page 1 of 1
DATED : May 6, 2003
INVENTOR(S) : Watanabe et al.

It is certified that error appears in the above-identified patent and that said Letters Patent is hereby corrected as shown below:

<u>Title page,</u>
Item [75], Inventors, change "Kazushi Nakashima, Kasuagi" to be -- Kazushi Nakashima, Kasugai --

Signed and Sealed this

Sixteenth Day of September, 2003

JAMES E. ROGAN
*Director of the United States Patent and Trademark Office*